(12) United States Patent
Buisker et al.

(10) Patent No.: US 6,566,670 B1
(45) Date of Patent: May 20, 2003

(54) METHOD AND SYSTEM FOR GUIDING A WEB OF MOVING MATERIAL

(75) Inventors: Raymond A. Buisker, Madison, WI (US); Andrew Kalnajs, Madison, WI (US)

(73) Assignee: Accuweb, Inc., Madison, WI (US)

( * ) Notice: Subject to any disclaimer, the term of this patent is extended or adjusted under 35 U.S.C. 154(b) by 0 days.

(21) Appl. No.: 09/548,800

(22) Filed: Apr. 14, 2000

Related U.S. Application Data (60) Provisional application No. 60/197,013, filed on Apr. 13, 2000.

(51) Int. Cl.[7] .............................................. G01N 21/17
(52) U.S. Cl. .......................... 250/559.36; 250/559.44; 356/237.2
(58) Field of Search .................... 250/559.44, 559.36, 250/222.2, 222.1, 226, 559.32, 559.06, 559.4, 559.29, 559.24, 559.22; 356/237.5, 237.2, 238.1, 238.2, 239.7, 239.8, 237.3

(56) References Cited

U.S. PATENT DOCUMENTS

| | | | |
|---|---|---|---|
| 4,806,776 A | * | 2/1989 | Kley ...................... 250/559.24 |
| 4,848,632 A | | 7/1989 | Mack et al. |
| 5,021,674 A | | 6/1991 | Brunner |
| 5,072,414 A | | 12/1991 | Buisker et al. |
| 5,166,532 A | | 11/1992 | Brunner et al. |
| 5,274,573 A | | 12/1993 | Buisker et al. |
| 5,803,334 A | | 9/1998 | Patel et al. |
| 5,813,337 A | | 9/1998 | Peters et al. |
| 5,834,877 A | | 11/1998 | Buisker et al. |

OTHER PUBLICATIONS

Brochure, *LED AccuBeam® Line/Edge Guide Control System*, AccuWeb, Inc., Madison, Wisconsin, undated.
Brochure, *BST–Controller with MicroProcessor Technology, CCD Line Guider—Basic Digital Controller for Line and Contrast Sensing Using CCD Camera*, BST Company, undated.
Brochure, *FE10 Opto–Electronic Line/Edge Detection System*, General Web Dynamics, Rockford, Illinois, 1984.

* cited by examiner

*Primary Examiner*—Robert H. Kim
*Assistant Examiner*—Hoon K. Song
(74) *Attorney, Agent, or Firm*—Brinks Hofer Gilson & Lione (57) ABSTRACT

A method and system for guiding a web of moving material is disclosed. The system includes a plurality of variable light sources that can project light onto the surface of the web. One light source or a combination of light sources can be selected to project light onto the web, and the wavelength of the light can be selected. A light detector receives light reflected from the surface of the web and generates a data signal in response to the light received. A controller can be used to analyze the reflected light to determine the position of the web of moving material. The system enables the lateral and/or longitudinal position of various types of webs to be efficiently and effectively determined based upon the position of a line, edge, or other mark disposed on the surface of the web.

34 Claims, 6 Drawing Sheets

METHOD AND SYSTEM FOR GUIDING A WEB OF MOVING MATERIAL

This application claims the benefit of U.S. Provisional Application No. 60/197,013, filed Apr. 13, 2000, entitled METHOD AND SYSTEM FOR GUIDING A WEB OF MOVING MATERIAL.

FIELD OF THE INVENTION

The present invention relates generally to guiding a web of moving material and more particularly to a system and method for determining the position of a web of moving material.

BACKGROUND

Many different types of materials including fabric, paper, films, foils, and the like are formed into what is commonly known as a web. In the production, processing, or treatment of a web, the web is often moving as it progresses from one operation, such as cutting, slitting, printing, and the like, to the next operation. It is important to be able to accurately determine the position of the web as it moves so that it can be properly aligned for the various operations. One commonly known technique for determining the position of a moving web involves detecting the position of the physical edge of the web using an edge detector. This is commonly referred to as edge guiding. Edge detectors typically include an optical or ultrasonic transmitter, which is placed on one side of the web, and a corresponding detector, which is placed on the opposite side of the web, that are used to detect the physical edge of the web. One such edge detector is described in U.S. Pat. No. 5,834,877 to Buisker et al.

Another technique for determining the position of a web involves detecting the position of a line appearing on the surface web. This is commonly known as line guiding. One method of line guiding involves using a light source to project light onto a surface of the web and using two photocells to receive light that is reflected off the surface. The amount of light received by each of the photocells can be compared to determine the position of the line on the surface of the web. In order for such a system to accurately determine the position of the line, there must be some appreciable contrast between the line and the background on both sides of the line that can be measured by the photocells.

However, in order to generate the necessary contrast, a light other than a white light may be required. For example, depending upon the relationship between the line and the associated background, other colors of light (i.e., light having a certain wavelength) may be required to achieve the necessary contrast. Also, if the web is made from film or other material that is sensitive to visible light, an infrared light source can be used to achieve the same results. Current line guiding systems do not allow different colored light to be projected as needed to effectively guide materials having different characteristics.

In addition, the position of the light source with respect to the light detector may vary depending upon the reflective properties of the web material. For example, if the web material has good reflective properties, as is the case with glossy or shiny metallic materials, the light source can be positioned in one location to achieve effective guiding. However, if the material has poor reflective materials, as is the case with paper or other materials having a matte finish, the light source can be placed in a different position in order to have effective guiding. Likewise, to achieve effective guiding from a material that has different reflective properties, such as holographic material, the light source can be placed in a third position. Current guiding systems to not provide the flexibility of light source configurations needed to effectively guide materials having different characteristics.

A system and method for guiding a web of moving material that overcome these deficiencies are needed.

DETAILED DESCRIPTION OF THE PRESENTLY PREFERRED EMBODIMENTS

By way of introduction, the preferred embodiments described below include systems and methods for guiding a web of moving material. These systems and methods enable the position of various types of webs to be determined based upon the position of a continuous or intermittent target line, a target edge of a pattern, or other marks that are disposed on the surface of the web. In one embodiment, a variable light source projects light onto the surface of the web of moving material. The color of the light or wavelength of the light can be selected based upon the type of material present in the web or upon the surface characteristics of the web material such as the color of the target line or edge and/or the background. A light detector receives light reflected from the surface of the web and generates a data signal that can be analyzed by a controller to determine the position of the target line, edge, or other mark. The position of the web can then be determined.

In another embodiment, a plurality of light sources are disposed at different positions to project light onto a surface of a web of moving material. One or more of the light sources can be selected to project light at a given time based upon the type of material present in the web or upon the reflective properties of the web material. A light detector can be used to receive light that is reflected from the surface of the web and a data signal can be generated in response to the received light. A controller can be used to analyze the reflected light to determine the position of the target line, edge, or other mark. The position of the web can then be determined. These systems enable the lateral and/or longitudinal position of various types of webs to be efficiently and effectively determined based upon the position of a line, edge, or other mark disposed on the surface of the web.

Figure 1:
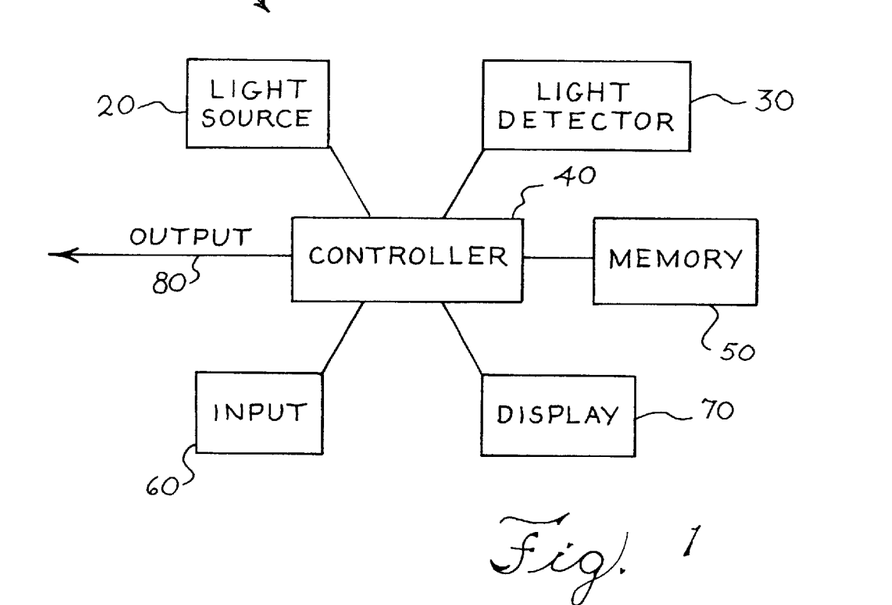
FIG. 1 is a block diagram of a detection system of a preferred embodiment.

By way of example, FIG. 1 depicts a system 10 of a preferred embodiment. The system 10 comprises a light source 20, a light detector 30, a controller 40, a memory 50, an input apparatus 60, a display 70, and an output port 80. The light source 20 is coupled with the controller 40 and is operable to project light onto a surface of a web of moving material (not shown). The term "coupled with," as used herein, means directly coupled with or indirectly coupled with through one or more components. The light source 20 preferably comprises a variable light source than can produce light having different colors. For example, the light source 20 can preferably produce red light, blue light, green light, and infrared light. Other colors and combinations of colors are possible, and virtually any color in the spectrum can be used depending upon the characteristics of the web. The light source 20 preferably comprises a plurality of variable light emitting diodes, but can comprise one or more other types of variable light sources.

The light detector 30 is coupled with the controller 40 and is operable to receive light that is reflected off the surface of the web. The light detector 30 is also operable to produce a data signal in response to the light received. This data signal can be used by the controller 40 to determine the lateral position of the web. The light detector 30 preferably comprises a plurality of photodiodes, but can comprise any suitable detector for receiving reflected light such as a charge-coupled device (CCD) or a CMOS imaging device or photodiode. CMOS imaging devices generally incorporate control circuits, such as amplifiers, integrators, clock generators, and shift registers on t the same die as the photodiodes, while CCD imaging devices require external control circuits that can add to the cost and complexity of a system.

The input apparatus 60 is coupled with the controller 40 and is operable to generate an input signal that can be received by the controller 40. The input apparatus 60 can be used to activate and deactivate the controller 40 and/or the system 10. The input apparatus 60 can also be used to change the functionality or settings of any parameters of the controller 40 and/or the system 10. The input apparatus 60 preferably comprises a keypad, but can comprise any form of input device such as a keyboard, a touch screen, one or more buttons or switches, or the like.

The display 70 is coupled with the controller 40 and is operable to provide a visual indication of the current system parameters or settings, alternative system options or settings, and current output data from the light detector 30, such as a contrast level. The display 70 preferably comprises a liquid crystal display, but can comprise any form of display such as a vacuum fluorescent display, an electro-luminescent display, a CRT display, a field-emission display, an LED display, or the like.

The output port 80 is coupled with the controller 40 and is operable to transmit an output signal from the system 10 to a controller or actuator that can be used to position the web. The output port 80 preferably comprises a seven-pin connector, but can comprise any suitable output connector.

The controller 40 is coupled with the light source 20, the light detector 30, the memory 50, the input apparatus 60, the display 70, and the output port 80. In the case of multiple light sources, the controller 40 is operable to control the selection of the light source or combination of light sources that project light at a given time. The controller 40 is also operable to control the color or wavelength of the light projected from the light source 20. The controller 40 can control the manner in which the light detector 30 detects light reflected from the surface of the web and the manner in which the light detector 30 generates a data signal in response to the received light.

The controller 40 can receive the data signal from the light detector 30 and can analyze the data signal to determine the position of the web. The controller 40 can also receive an input signal from the input apparatus 60 and can provide a display signal to the display 70. The controller 40 is preferably responsive to a software program than can be stored in the memory 50. The controller 40 preferably comprises a microcontroller, but can comprise any suitable controller, microprocessor, or processor, as known to those skilled in the art. The controller can be one or more than one component, as the functionality of the controller can be distributed among several components in the system 10.

Figure 2:
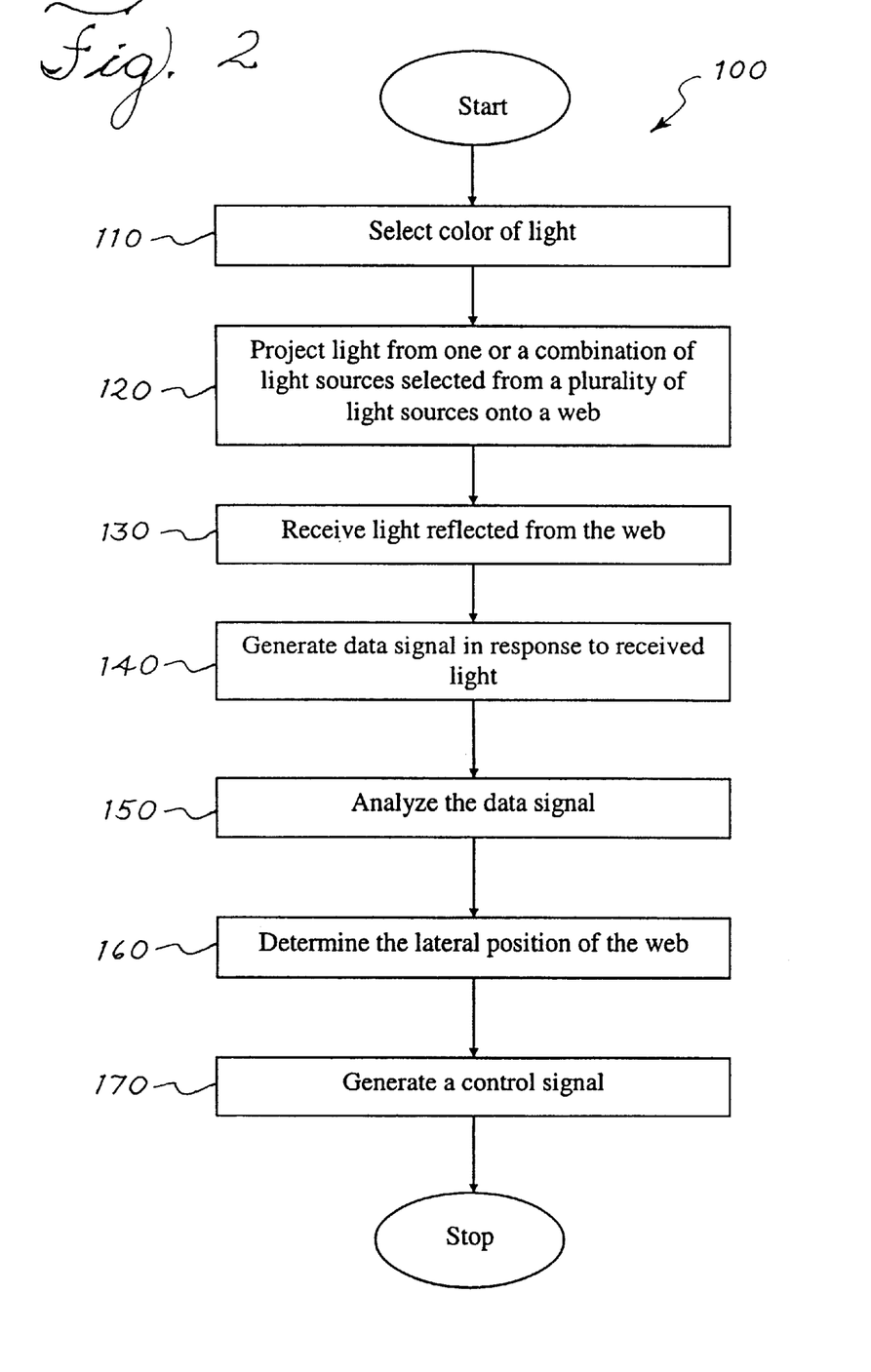
FIG. 2 is a flow chart of a method of a preferred embodiment for guiding a web of moving material.

The system 10 of FIG. 1 can be used to implement the method 100 depicted in FIG. 2. The color of the light that is to be projected from the light source 20 can be selected (act 110, FIG. 2). The color can be based upon, for example, the type of material in the web or the color of the target line, edge, or other mark and/or the background. One light source or a combination of light sources can be activated to project light onto a surface of a web (act 120). The specific light source or combination of light sources can be selected based upon, for example, the reflective characteristics of the web. The light detector 30 can receive light that is reflected off the surface of the web (act 130) and can produce a data signal (act 140) in response to the light received. The controller 40 can analyze the data signal (act 150) and determine the position of the web (act 160). A control signal can then be generated (act 170) that can be used to alter the position of the web.

Figure 3:
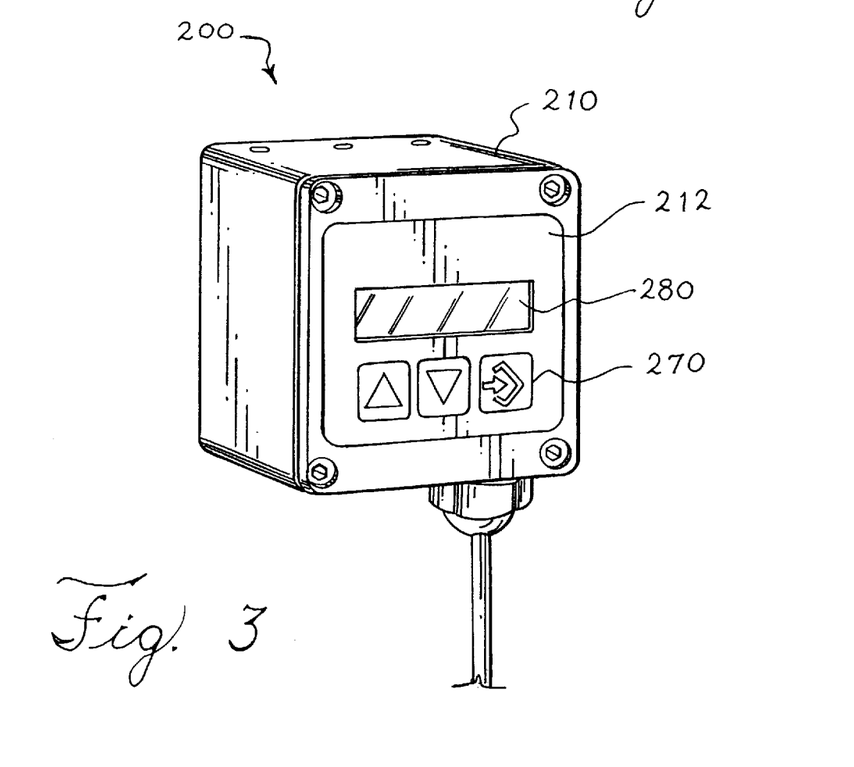
FIG. 3 is a front perspective view of a detection system of a preferred embodiment.
Figure 4:
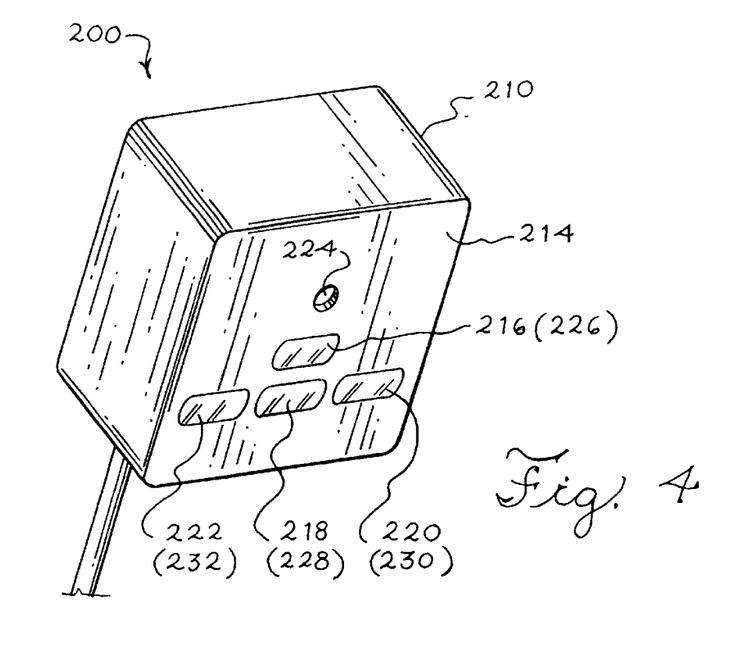
FIG. 4. is a rear perspective view of a detection system of a preferred embodiment.
Figure 5:
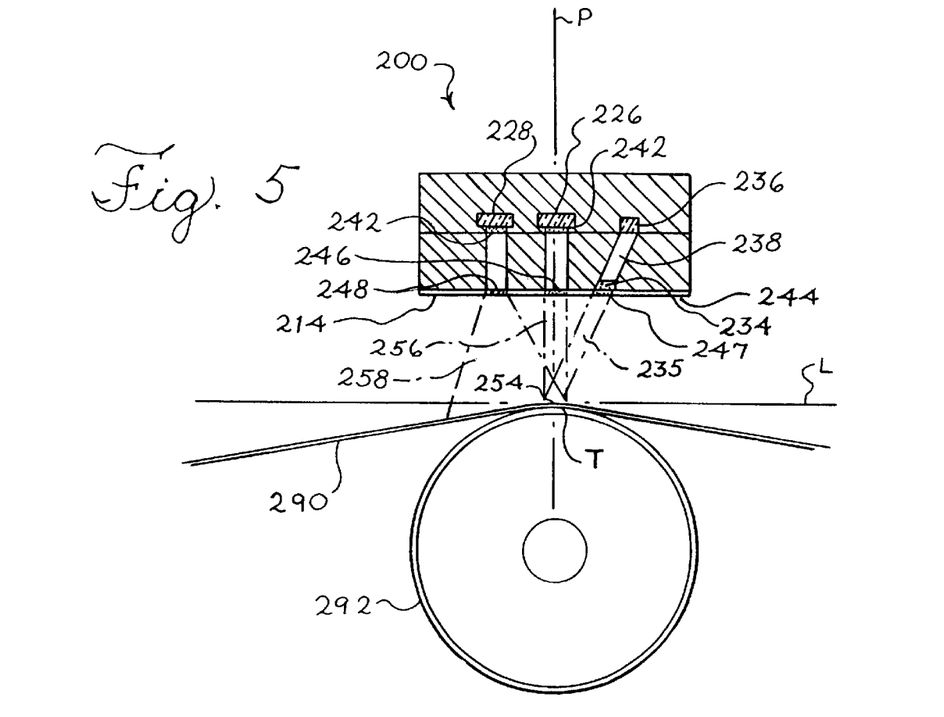
FIG. 5 is a sectional view of a detection system of a preferred embodiment.

By way of further example, FIGS. 3–5 depict a preferred embodiment of the system 10 described above. The system 200 comprises a housing 210 having a front side 212 and a back side 214. The back side of the housing 214 is preferably oriented parallel to a plane L that is tangent to a point of tangency T between the web 290 and backup roller 292. The back side of the housing 214 is preferably located one inch above the plane L. A black anodized coating is preferably applied to all surfaces of the housing 210 to protect the housing 210 from corrosion and to absorb stray light.

First, second, third, and fourth light ports 216, 218, 220, 222 are disposed on the back side of the housing 214. The first and second light ports 216, 218 are preferably longitudinally disposed adjacent one another with the first light port 216 being positioned approximately 0.577 inches above the second light port 218. The third and fourth light ports 220, 222 are preferably laterally disposed with respect to the first and second light ports 216, 218, with the third light port 220 being positioned to one side of the first and second light ports 216, 218 and the fourth light port 222 being positioned to the opposite side of the first and second light ports 216, 218. A detector port 224 is also disposed on the back side of the housing 214. The detector port is preferably longitudinally disposed approximately 0.577 inches above the first light port 216. A polyester or Mylar film 244 (FIGS. 5–6) can be applied to cover the back side 214 of the housing to further protect the components included therein.

First, second, third, and fourth light sources 226, 228, 230, 232 are disposed within the housing 210 and are optically coupled with the first, second, third, and fourth light ports 216, 218, 220, 222, respectively, by four light channels. The first, second, third, and fourth light sources 226, 228, 230, 232 preferably comprise light emitting diodes that are able to produce light having different colors or wavelengths. In one embodiment, the light emitting diodes are able to produce red, green, blue, and infrared light, which are each preferred for different applications as described herein. The preferred wavelength of red light is 660 nm, the preferred wavelength of green light is 525 nm, the preferred wavelength of blue light is 468 nm, and the preferred wavelength of infrared light is 940 nm. One example of a variable light emitting diode is the RGB-1001-001, which is commercially available from Leadtronics, Inc. Other colors of light, wavelengths of light, and/or combinations of light can be used. Also, other light sources having greater or lesser brightnesses can also be used. For example, a cluster of light emitting diodes or one or more lasers can be used to project light. The first, second, third, and fourth light sources 226, 228, 230, 232 can be surrounded by a strip of reflective material to effectively channel light from the light sources to the light channels. This prevents light from escaping through any gaps between the light channels and the light sources.

A diffuser 242 is preferably placed in front of the first, second, third, and fourth light sources 226, 228, 230, 232 at one end of the light channels. The diffuser 242 diffuses the light projected from the light sources which, in the case of light emitting diodes, tends to be focused into a narrow beam of light. The diffuser 242 produces a wider beam of light than the one projected from the light sources. One suitable diffuser is the holographic light shaping diffuser, part number LSD 60PE5F10, commercially available from Physical Optics Corporation. The light channels channel the light from the light sources 226, 228, 230, 232 and direct the light to the light ports 216, 218, 220, 222. The interior surfaces of the light channels are preferably coated with an opaque white material that preferably has diffuse reflection characteristics to enhance the projection of light from the light sources 226, 228, 230, 232 and to prevent the interior of the light channel from absorbing light. The light channels are preferably disposed substantially perpendicular to plane L.

Figure 6:
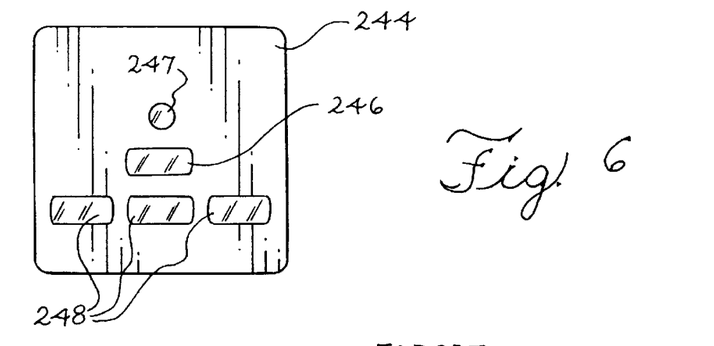
FIG. 6 is a front view of a protective film of a preferred embodiment.

A clear plastic window 246 is preferably formed in the film 244 and is located over the end of the light channel opposite the first light source 226. The clear plastic window 246 is placed over the first light port 216 to prevent contamination of the internal portion of the light port. The clear plastic film 246 does not further diffuse the light and produces a focused beam of light 256. A plurality of translucent white windows 248 are preferably formed in the film 244 and are located over the end of the light channels opposite the second, third, and fourth light sources 228, 230, 232. The translucent white windows are placed over the second, third, and fourth light ports 218, 220, 222 and serve to diffuse the light projected from the second, third, and fourth light sources 228, 230, 232 and to prevent contamination of the internal portions of the light ports. The translucent white windows 248 diffuse the light and produce a relatively wide beam of light 258. This causes a portion of the light to be projected onto the focal area 254 of the focusing lens 234, which enables detection of the target line, edge, or other mark as described in more detail below. One suitable translucent white material is Valox, which is commercially available from General Electric.

The light from the light sources 226, 228, 230, 232 can be diffused or otherwise projected onto the focus area 254 in other ways as well. For example, the light channels and/or the light sources 226, 228, 230, 232 can be disposed at one or more angles with respect to the surface of the web 290. This serves to direct the light to the focus area 254 more efficiently. Also, a lens or film that alters the direction of the light projected from the light sources can be used to direct light to the focus area 254.

In operation, the first, second, third, and fourth light sources 226, 228, 230, 232 preferably project a blue light as the preferred default setting. However, if the target line, edge, or mark is blue, a color other than blue may be preferred in order to achieve a desired contrast necessary to detect the target line, edge, or mark. In such a case, a red light or green light can be used. An infrared light is preferred for guiding on a photographic film or other material that is sensitive to visible light.

Figures 7, 8, 9:
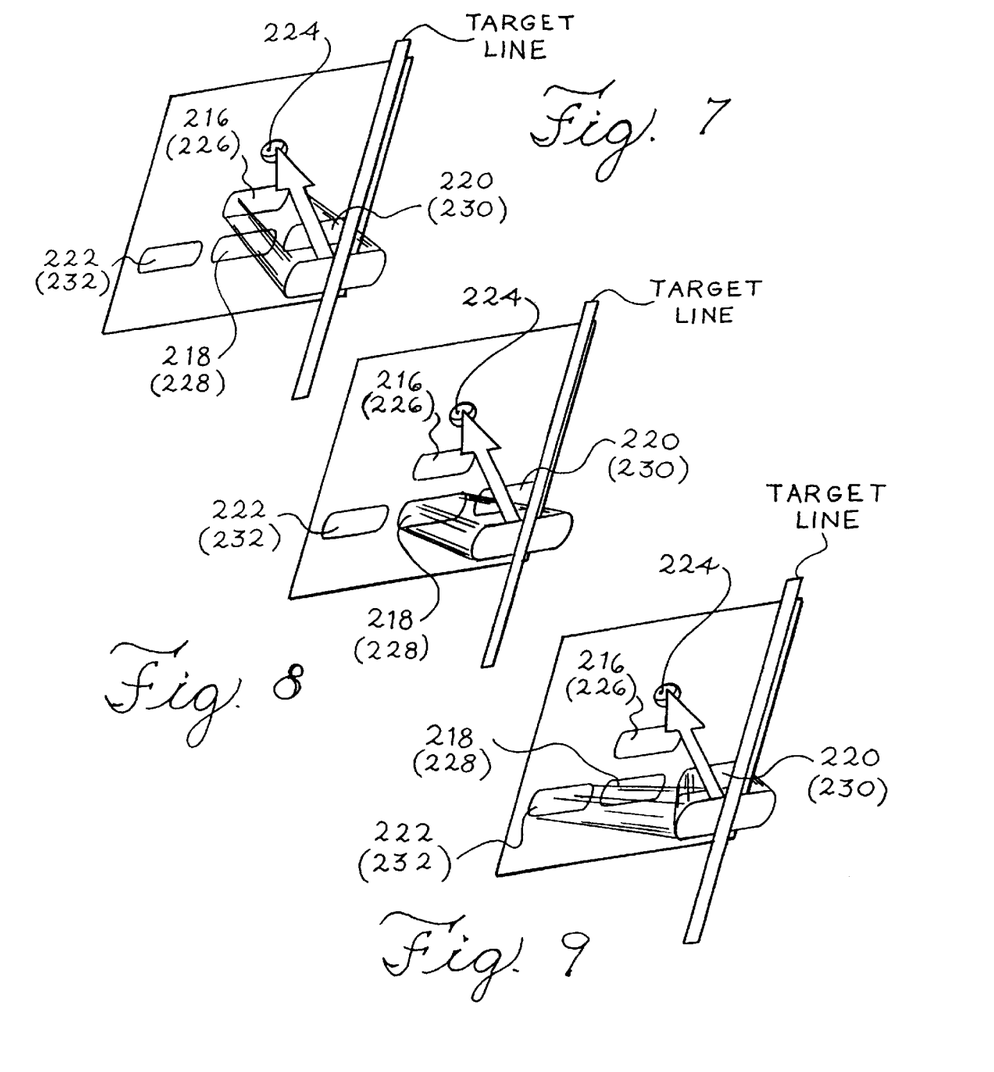
FIG. 7 is a rear perspective view of a detection system of a preferred embodiment operating in a first mode.
FIG. 8 is a rear perspective view of a detection system of a preferred embodiment operating in a second mode.
FIG. 9 is a rear perspective view of a detection system of a preferred embodiment operating in a third mode.

One or more of the first, second, third, and fourth light sources 226, 228, 230, 232 can project light at a given time. For example, as shown in FIGS. 7–8, either the first or second light source 226, 228 can alone project light. The first light source 226 is preferably selected when the web material comprises a matte material that has diffuse reflection characteristics because first light source 226 provides an optimum angle of illumination upon the web 290. Because a matte material has diffuse reflection characteristics, it will tend to scatter reflected light in all directions, including towards the focusing lens 234. Selection of the first light source 226 directs more light onto the focal area 254 than the other light sources because the first light port 216 is closest to the focal area 254 and is located directly above the focal area 254. Projecting light in this manner causes sufficient light to be reflected along the optical axis of the focusing lens 234 and results in better detection for matte material. The first light source 226 can also be used on holographic material when guiding on the edge of a holographic image or on a line, edge, or mark that has diffuse reflection characteristics.

The second light source 228 is preferably selected for sensing a target line, edge, or mark on a web material that has a glossy or mirror-like finish because the second light source 228 provides an optimum angle of illumination upon the web 290. Selection of the second light source 228 causes light to be projected from the second light port 218. While light is not projected directly onto the focal area 254 because the light channel is perpendicular to the plane L, some light is projected onto the focal area 254 as a result of the diffusion of light caused by the translucent white window 248 located over the second light port 218. Since the glossy web material has specular reflection characteristics, an out-of-focus image of the second light port 218 is reflected from the web 290 onto the photodiodes 236, and this image fills the entire field of view of the photodiodes 236. The target line, edge, or mark, located at the focal area 254 is, by definition, in focus. The combined image that is in turn projected onto the photodiodes 236 is that of a dark line, edge, or mark surrounded by a bright, uniformly lit background. This effect is a result of the geometric relationship between the positions and orientations of the second light port 218, the focal area 254, and the detector port 224.

Light emitted from the second light port 218 towards the focal area 254 strikes the focal area 254 at a 30 degree angle of incidence and is reflected at a 30 degree angle of reflectance towards the detector port 224 along the optical axis 235 of the focusing lens 234. A target line, edge, or mark in the focal area 254 on the web 290 is, by definition, in focus, but the optical path from the second light port 218 to the photodiodes 236 is twice the length of the path from the focal area 254 to the photodiodes 236, so the second light port 218, according to the rules of optics, is out of focus. To ensure uniform projection of the second light source 228 onto photodiodes 236, the size of the second light port 218 is more than twice the size of the focal area 254. This results in better detection for glossy or highly reflective material.

Alternatively, as shown in FIG. 9, the third and fourth light sources 230, 232 can simultaneously project light. This combination of light sources is preferred when sensing a target line, edge, or mark on a web that comprises holographic or similar material because these types of materials reflect most of the incident light at angles other than may be expected from pure diffuse or specular surfaces. Selection of the third and fourth light sources 230, 232 causes light to be projected from the third and fourth light ports 220, 222. Because these ports 220, 222 are located in a different vertical plane than the optical axis 235 of the focusing lens and because these ports 220, 222 project light nearly perpendicular to the plane L, the majority of the light is not projected directly onto the focal area 254. However, a portion of the light reaches the focusing lens 234 and ultimately the photodiodes 236 as a result of the diffusion of light from the light sources and as a result of the reflective properties of the web material. The translucent white windows 248 covering the third and fourth light ports 220, 222 scatter some light towards the focal area 254. Also, microprism or other light-directing structures present in the web material deflect light towards the focusing lens 234. This results in better detection for holographic or other similar material.

A focusing lens 234 is disposed within the detector port 224 for focusing the light reflected off the surface of the web 290. A clear window 247 is preferably located within the film 244 and is positioned over the focusing lens 234 to protect the lens. The focusing lens 234 preferably produces a focal area 254 that is preferably ⅝" in diameter. The focusing lens 234 focuses and directs light from the focal area 254 on the surface of the web 290 to the plurality of photodiodes 236. The focusing lens 234 is preferably 6.25 mm in diameter with a 12.5 mm focal length. One suitable focusing lens is the model #45398 available from Edmund Scientific. The focal distance of the system 200 is preferably one inch from the surface of the web 290 to backside of the housing 214.

A plurality of photodiodes 236 are disposed within the housing 210 and a detector channel 238 connects the focusing lens 234 and the photodiodes 236. The detector channel 238 is preferably formed at an angle of 30 degrees with respect to a line P that is perpendicular to the plane of the back side 214 of the housing and perpendicular to the plane L. Other angles can also be used. Each one of the plurality of photodiodes 236 receives light reflected from the surface of the web 290. In turn, each one of the plurality of photodiodes 236 generates a voltage signal that varies in response to the amount of light received by that photodiode. The voltage is preferably generated through the use of an integrator that accumulates a voltage charge during the exposure time of the photodiodes 236. The exposure time generally refers to the amount of time that the photodiodes 236 receive light before being reset and is related to the scan rate which generally refers to frequency at which the photodiodes are reset. In this embodiment, the exposure time is preferably between 4 milliseconds and 50 milliseconds. Accordingly, the photodiodes 236 receive light and accumulate a voltage charge for 4 milliseconds to 50 milliseconds before being reset. The plurality of photodiodes 236 preferably comprises a 128×1 array of photodiodes such as the TSL1401, which is commercially available from Texas Advanced Optoelectronic Solutions. Other components can also be used to receive the reflected light. For example, photodiodes having a greater or lesser sensitivity can be used in place of the photodiodes 236. Also, components have a greater or lesser exposure time can also be used such that the scan rate can be increased or decreased.

The photodiodes 236 and light sources 226, 228, 230, 232 are preferably located on a single printed circuit board and are thus located in approximately the same horizontal plane. The linear axis of the photodiode array is preferably parallel to the plane L and the major axis of the photodiodes is preferably perpendicular to the web 290 and perpendicular to the target line, edge or portion of the mark. The distances between the photodiodes 236, the focusing lens 234, and the focal area 254 are governed by two factors. The first is that a focused image of the focal area 254 is projected upon the photodiodes 236. The second is that the size of the focused image is reduced to match the size of the photodiodes 236. Since the photodiodes are preferably arranged in a one-dimensional array and the focal area 254 is also one-dimensional, in this example only the length of the array and length of the required focal area are considered when calculating the required reduction in image size. The required focal area is 0.625 inches long and the photodiode array is 0.320 inches long, so the required reduction factor is approximately 0.5. The exact distances between the photodiodes 236, the focusing lens 234, and the focal area 254 can be determined based on the reduction factor.

A controller (not shown) is preferably disposed within the housing 210 and is coupled with the first, second, third, and fourth light sources 226, 228, 230, 232, the plurality of photodiodes 236, a memory (not shown), a keypad 270 and the display 280. The controller preferably comprises a 20 MHz microcontroller such as the #PIC16C77-20I/L, which is commercially available from Microchip Technologies, and which includes an analog-to-digital converter, a timer, random access memory, read only memory and other peripherals. The controller can control the selection of the color of light projected by the light sources. The controller can also control which light source or combination of light sources project light at a given time.

The controller can receive the data signal generated by the plurality of photodiodes 236 and can analyze the data signal to determine the lateral position of the web. To determine the lateral position of the web, the controller attempts to identify differences in the voltage output of photodiodes that are located adjacent to one another. Such differences in voltages can indicate a transition from light to dark and thus signify the presence of a line, edge, or mark. For example, where one photodiode has a relatively low voltage as compared to the voltage from an adjacent photodiode, there is a contrast in the light received. This indicates that there is a contrast on the surface of the web of material off of which the light is reflected, and a contrast on the surface of the web indicates that an edge is present. The controller can also control a minimum level of contrast that is required in order for the controller to determine that an edge is present.

The edge can be the target edge of a pattern or one edge of the target line or mark. In general, the controller can detect transitions from light to dark and dark to light, which signify an edge or mark and can also detect transitions from light to dark to light and dark to light to dark, which signify a line or mark. This can be done in accordance with an edge identifying algorithm such as the one disclosed in Appendix A attached hereto, which identifies edges while filtering out anomalies. The controller can also control the order in which the data received from the photodiodes 236 is analyzed. This can involve altering the scanning direction, which can be from left to right or right to left.

The controller can also be set to prevent erroneously guiding off an improper line, edge, or mark. This is of particular concern when a plurality of lines, edges, or marks are in close proximity. The controller can be set to look for a maximum and minimum margin to the left of the target line, edge, or mark. This will prevent guiding a line, edge, or mark that does not meet this requirement. The controller can also be set to look for a maximum and, minimum line width. This will prevent guiding a line that is too wide or too narrow. The controller can be set to look for a maximum and minimum margin to the right of the target line, edge, or mark. This will prevent guiding a line or edge that does not meet this requirement.

In a preferred embodiment, the unit of measure used in setting these maximum and minimum values is preferably a "half-pixel". Where the entire length of the focal area 254 is 0.625 inches and must be projected onto the photodiodes 236, which is composed of 128 discrete photodiodes or pixels, each pixel corresponds to a linear distance of 0.00488 inches at the focal area 254 on the web. Accordingly, each half pixel corresponds to a linear distance of 0.00244 inches. The unit of measure used in the controller can be varied based upon the size of the focal area and the number and arrangement of the photodiodes.

The controller can also control the scan rate and exposure time of the photodiodes 236. The scan rate is preferably set so that the voltage produced by the most brightly illuminated pixel in the photodiodes 236 is approximately equal to 90 percent of an input voltage such as the full-scale input voltage of an analog-to-digital converter coupled with the controller. Each pixel is preferably represented by a photodiode and an integrator. The integrator can integrate current generated by an associated photodiode in response to incident light and can generate an output voltage proportional to the integrated current. Varying the scan rate directly varies the integration time, which varies the integrator's peak output voltage. Accordingly, the scan rate can be decreased and the exposure time increased if the voltage produced by the most brightly illuminated pixel is less than 90 percent. Conversely, the scan rate can be increased and the exposure time decreased if the voltage produced by the most brightly illuminated pixel is greater than 90 percent.

All of these functions of the controller can be controlled by a software program that is implemented in the controller. One suitable software program is the C language program listed in Appendix A, which is attached hereto. The program can be stored in memory included within the controller or it can be stored in an external memory. The controller can also store a number of preset combinations of parameters, such as color of light, selected light source, etc., for easy access by a user. This data can be stored in the memory included within the controller or in a memory such as an EEPROM. Storing these combinations of parameters is especially useful when changing from one type of web to another. Instead of entering all of the parameters each time a change is made, a set of stored parameters can be recalled from memory and implemented without requiring a user to input each parameter.

The display 280 is preferably disposed on the front side of the housing 212 and is coupled with the controller. The display 280 preferably comprises a 2 line by 16 character liquid crystal display such as the MDLS-16265C-G-LV-LED4G, which is commercially available from Varitronix. The display 280 provides a visual indication of settings and can also be used to present options to a user. For example, the display 280 can be used to provide a visual indication of the location of lines, edges, or marks that are being detected by the system 200. However, in a preferred embodiment, the display 280 is not large enough to depict the entire field of view of the plurality of photodiodes 236. Accordingly, a zoom setting, such as 1x, 2x, 4x, etc., can be selected so that only a portion of the field of view is displayed.

The keypad 270 is preferably disposed on the front side of the housing 212 and is coupled with the controller. The key pad 270 enables a user to provide input to the system. For example, a user can provide input to change settings or select information from the menu as described above. Such changes in settings can include changes in the light sources, changes in the color of light transmitted by the light source (s), and changes in the scan direction of the controller. The keypad 270 preferably comprises a three button custom keypad from Delta Technologies, Inc.

While the light sources and plurality of photodiodes are shown within a single housing, they can be incorporated in separate housings. The arrangement of the light sources can be changed or varied and additional or fewer light sources can be used. Also, a remote control panel and/or a remote display can be used in conjunction with the system. An RS485 interface, for example, can be used to couple a remote control panel and/or a remote display with the controller.

Figure 10:
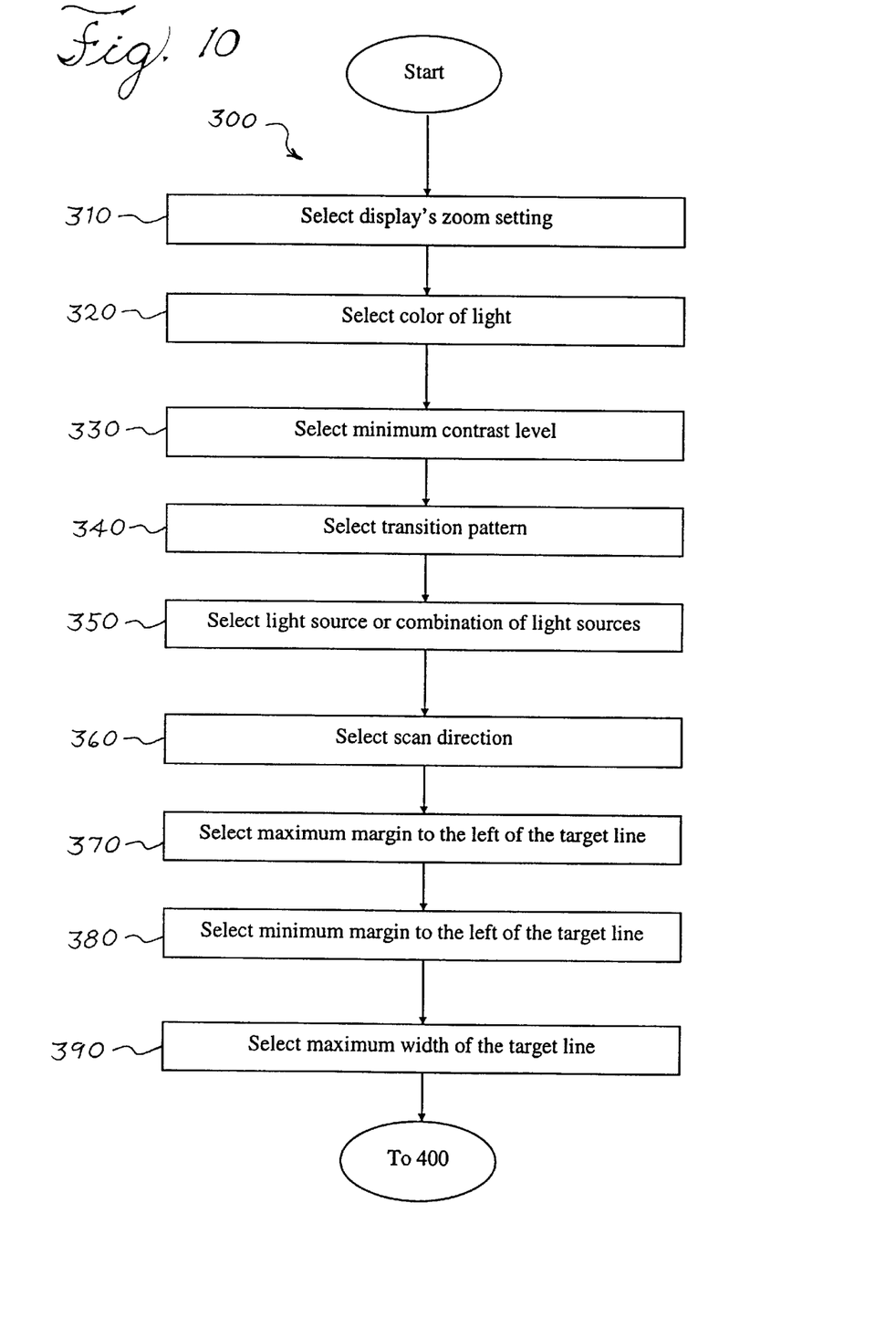
FIG. 10 is a more detailed flow chart of the method of guiding a web of moving material depicted in FIG. 1.

The system depicted in FIGS. 3–9 can be utilized to implement the method 300 depicted in FIG. 10. For purposes of illustration, assume that the web is made up of a paper material that has a white matte finish and that includes a red line on which the web is to be guided. This line is 0.1 inches wide with 0.5 inches of clear space to the left of the line and with 0.25 inches of clear space to the right side of the line. Also assume that the system 200 has been positioned opposite a backup roller that supports web. The optical axis of the first light source should be aligned with the center of the backup roller, and the focal area should focused on the point T. Also assume that the system 200 is located 1 inch above the surface of the web. The optical axis of the first light source should also be positioned to project light on the target line, edge, or mark, and the focal area should focused on the target line, edge, or mark.

After the system 200 has been setup as described above, a zoom setting, such as 1x, can be selected for the display (act 310, FIG. 10). A blue light can be selected as the color to be transmitted (act 320). A minimum acceptable contrast level can be selected (act 330). A light to dark to light transition pattern can then be selected (act 340). The first light source can then be selected to project light (act 350). A left to right scan direction can also be selected (act 360). In addition, a maximum margin to the left of the target line can be selected (act 370). A minimum margin to the left of the target line or edge can be selected (act 3 80). A maximum width of the target line can be selected (act 390). A minimum width of the target line can also be selected (act 400). A maximum margin to the right of the target line can be selected (act 410). A minimum margin to the right of the target line can also be selected (act 420).

Light can then be projected onto the surface of the web using the first light source (act 430). The light is reflected off the surface of the web and is received by the photodiodes (act 440). The photodiodes produce a data signal in response to the received light (act 450). The data signal preferably comprises a plurality of discrete voltages, one for each photodiode, that vary based upon the amount of light received by that photodiode. The controller can receive the data signal (act 460) and can analyze the data signal (act 470) to determine the lateral position of the target line. The controller can produce a control signal (act 480) that can be transmitted to a controller or actuator to alter the lateral position of the web.

The act of analyzing the data signal (act 470, FIG. 10) preferably comprises the act of determining the lateral position of the web, or determining the longitudinal position of the web. The acts of selecting different parameters (acts 310–420, FIG. 10) can be done automatically in response to a predetermined selection criteria or can be done manually by a user. When the web material changes, the system 200 can be readily configured to guide the new material without altering the physical setup described above. The system can be reconfigured by changing the color of light projected by the light sources and/or the pattern of light sources projecting light at a given time. For example, if the material were changed from paper having a matte finish to paper having a glossy finish, the second light source could be selected instead of the first light source. Also if the target line changed from a red line on a white background to a blue line on a yellow background, the color of the light could be changed from blue to red. Additional parameters could also be changed as necessary.

In typical applications the system 200 is mounted in either a vertical or horizontal configuration. In both configurations the shape and color of the housing and the location and angle of the detector port's optical axis minimize the amount of ambient light entering the detector port. Excessive ambient light of the wrong color or angle of incidence may reduce the system's ability to discriminate between a colored target line, edge, or mark and background, or between a glossy line or edge and matte background, or vice versa.

In a vertical mounting configuration the back side of the housing is perpendicular to the floor with the detector port located above the light ports. In this mounting configuration the optical axis of the detector port is oriented at an angle of 30 degrees below horizontal, and the plane tangent to the point of tangency between the web and backup roller is also perpendicular to the floor. Some of the light emitted by overhead lighting fixtures may strike the web at the focal area. If the web material has specular reflection characteristics then all of the overhead light striking the web at the focal area will be reflected downward towards the floor, and none of it will enter the detector port. If the web material has diffuse reflection characteristics then most of the overhead light striking the web at the focal area will be reflected towards the floor, and the light scattering properties of web material will reflect only a small proportion of the light upward into the detector port.

In a horizontal mounting configuration the system is positioned above the web so that the back side of the housing is parallel to the floor and faces the web and floor, and the plane tangent to the point of tangency between the web and backup roller is also parallel to the floor. In this mounting configuration the large, square shape of the back side of the housing, its non-reflective black color, and proximity to the web shield the focal area from a substantial proportion of the light emitted by overhead lighting fixtures.

It is to be understood that a wide range of changes and modifications to the embodiments described above will be apparent to those skilled in the art and are contemplated. It is therefore intended that the foregoing detailed description be regarded as illustrative rather than limiting, and that it be understood that it is the following claims, including all equivalents, that are intended to define the spirit and scope of the invention.

We claim:

1. A system for guiding a web of moving material the system comprising:

a first light source oriented to project light onto a surface of the web of moving material, the first light source being operable to project a plurality of selectable wavelengths of light;

a second light source oriented to project light onto the surface of the web of moving material, the second light source being operable to project a plurality of selectable wavelengths of light;

a plurality of photodiodes oriented to receive light reflected from the surface of the web of moving material, the plurality of photodiodes being operable to generate a data signal in response to the light received; and a controller operable to generate a control signal in response to the data signal, the control signal comprising an indication of a position of the web of moving material, wherein the first light source and the second light source can be selected to project light in response to a first selection criteria and the first and second light sources do not project light simultaneously, and a wavelength of the projected light can be selected in response to a second selection criteria.

2. The system of claim 1, wherein the first and second light sources comprise light emitting diodes.

3. The system of claim 1, wherein the first and second light sources are operative to transmit light selected from the group consisting of red light and blue light.

4. The system of claim 1, wherein the first and second light sources are operative to transmit light selected from the group consisting of red light, blue light, and infrared light.

5. The system of claim 1, wherein the second light source is disposed longitudinally adjacent to the first light source.

6. The system of claim 1, wherein the plurality of photodiodes comprises an array of photodiodes.

7. The system of claim 1, wherein the plurality of photodiodes comprises a 128 by 1 array of photodiodes.

8. The system of claim 1, further comprising a third light source oriented to project light onto the surface of the web of moving material, the third light source being operable to project a plurality of selectable wavelengths of light.

9. The system of claim 8, wherein the third light source is laterally disposed from the first light source.

10. The system of claim 8, wherein the third light source comprises a light emitting diode.

11. The system of claim 8, wherein the third light source is operative to transmit light selected from the group consisting of red light and blue light.

12. The system of claim 8, wherein the third light source is operative to transmit light selected from the group consisting of red light, blue light, and infrared light.

13. The system of claim 1, wherein the controller is operable to determine a lateral position of the web of moving material.

14. The system of claim 1, wherein the controller is operable to determine a longitudinal position of the web of moving material.

15. The system of claim 1, further comprising a detector channel disposed between the plurality of photodiodes and the web of moving material and the detector channel is oriented at approximately 30 degrees with respect to a line perpendicular to the surface of the web of moving material.

16. A method for guiding a web of moving material, the method comprising:

(a) providing a plurality of light sources oriented to project light onto a surface of the web of moving material, the plurality of light sources being operable to project a plurality of selectable wavelengths of light;

(b) projecting light from one of the plurality of light sources onto the surface of the web of moving material in response to a first selection criteria, the light having a wavelength that is selected in response to a second selection criteria;

(c) receiving light reflected from the surface of the web of moving material;

(d) analyzing the reflected light to determine a position of the web of moving material.

17. The method of claim 16, wherein (b) comprises projecting red light onto the surface of the web of moving material.

18. The method of claim 16, wherein (b) comprises projecting blue light onto the surface of the web of moving material.

19. The method of claim 16, wherein (b) comprises projecting infrared light onto the surface of the web of moving material.

20. The method of claim 16, wherein (c) comprises generating a data signal in response to the light received.

21. The method of claim 16, wherein (d) comprises determining a lateral position of the web of moving material.

22. The method of claim 16, wherein (d) comprises determining a longitudinal position of the web of moving material.

23. A method for guiding a web of moving material, the method comprising:

(a) selecting a light source to project light onto a surface of the web of moving material from a plurality of light sources in response to a first selection criteria;

(b) selecting a color of light to be projected from the selected light source in response to a second selection criteria;

(c) projecting light from the light source onto the surface of the web of moving material;

(d) receiving light reflected from the surface of the web of moving material;

(e) analyzing the reflected light to determine a position of the web of moving material.

24. A system for guiding a web of moving material comprising:

a first light source oriented to project light onto a surface of the web of moving material, the first light source being operable to project a plurality of selectable wavelengths of light;

a second light source oriented to project light onto the surface of the web of moving material, the second light source being longitudinally disposed adjacent the first light source and being operable project a plurality of selectable wavelengths of light;

a third light source oriented to project light onto the surface of the web of moving material, the third light source being laterally disposed to a first side of the first or second light sources and being operable project a plurality of selectable wavelengths of light;

a fourth light source oriented to project light onto the surface of the web of moving material, the fourth light source being laterally disposed to a second side of the first or second light sources and being operable to project a plurality of selectable wavelengths of light;

a plurality of photodiodes oriented to receive light reflected from the surface of the web of moving material, the plurality of photodiodes be operable to generate a data signal in response to the light received; and a controller operable to generate a control signal in response to the data signal, the control signal providing an indication of the position of the web of moving material, wherein the first and second light sources can be selected to project light in response to a first selection criteria and the first and second light sources do not project light simultaneously, and a wavelength of the projected light can be selected in response to a second selection criteria.

25. The system of claim 24, wherein the first, second, third, and fourth light sources comprise light emitting diodes.

26. The system of claim 24, wherein the first, second, third, and fourth light sources are operative to transmit light selected from the group consisting of red light and blue light.

27. The system of claim 24, wherein the first, second, third, and fourth light sources are operative to transmit light selected from the group consisting of red light, blue light, and infrared light.

28. The system of claim 24, wherein the plurality of photodiodes comprises an array of photodiodes.

29. The system of claim 1, wherein the first and second light sources are operative to transmit light selected from the group consisting of red light, blue light, green light, and infrared light.

30. The method of claim 16, further comprising:

(e) determining a position of the web of moving material; and (f) generating a control signal that comprises an indication of the position of the web of moving material.

31. The method of claim 30, further comprising:

(g) altering the position of the web of moving material in response to the control signal.

32. The method of claim 23, further comprising:

(f) generating a control signal that comprises an indication of the position of the web of moving material.

33. The method of claim 32, further comprising:

(g) altering the position of the web of moving material in response to the control signal.

34. The system of claim 24, wherein the first, second, third, and fourth light sources are operative to transmit light selected from the group consisting of red light, blue light, green light, and infrared light.

* * * * *